US00PP33799P2

(12) United States Plant Patent
Bull

(10) Patent No.: US PP33,799 P2
(45) Date of Patent: Dec. 28, 2021

(54) ***ECHINACEA* PLANT NAMED 'BULLECHIPUR 1201'**

(50) Latin Name: *Echinacea purpurea*
Varietal Denomination: BullEchipur 1201

(71) Applicant: Hartwig Bull, Gönnebek (DE)

(72) Inventor: Hartwig Bull, Gönnebek (DE)

(73) Assignee: Hartwig Bull, Gönnebek (DE)

( * ) Notice: Subject to any disclaimer, the term of this patent is extended or adjusted under 35 U.S.C. 154(b) by 0 days.

(21) Appl. No.: 17/408,613

(22) Filed: Aug. 23, 2021

Related U.S. Application Data

(60) Provisional application No. 63/103,822, filed on Aug. 26, 2020.

(51) Int. Cl.
*A01H 5/02* (2018.01)
*A01H 6/14* (2018.01)

(52) U.S. Cl.
USPC ..... Plt./428
CPC ..... *A01H 6/1448* (2018.05)

(58) Field of Classification Search
USPC ..... Plt./428
CPC ..... A01H 5/02
See application file for complete search history.

(56) References Cited

PUBLICATIONS www.gobotany.nativeplanttrust.org/species/Echinacea/purpurea/; Sep. 30, 2021; 4 pages.*

* cited by examiner

*Primary Examiner* — Kent L Bell
(74) *Attorney, Agent, or Firm* — The Webb Law Firm

(57) ABSTRACT

A new and distinct variety of *Echinacea* plant having a compact growth habit and numerous, wine red colored blooms.

3 Drawing Sheets

Botanical classification: *Echinacea purpurea.*
Varietal denomination: 'BullEchipur 1201'.

BACKGROUND OF THE INVENTION

The present invention comprises a new and distinct cultivar of *Echinaces* plant known by the varietal name 'BullEchipur 1201'. The new variety was discovered in August of 2017 in Gönnebeck, Germany as the result of a planned breeding program with the purposes of providing *Echinaces* plants with a compact growth habit, increased flowers per plant, unique flower colors, clean foliage, large blooms, a faster crop time, and more uniformity when compared to prior *Echinaces* plants. The new variety is the result of a cross between an unpatented *Echinacea purpurea* variety having an internal breeder's reference of "BEP 27-2014" (female parent) and an unpatented *Echinacea purpurea* variety having an internal breeder's reference of "BEP 98-2014" (male parent) from the breeder's own collection. The new variety was first asexually reproduced via in-vitro tissue culture cuttings in Gönnebek, Germany in September of 2017. The new variety is similar to its parental varieties in botanical classification, but exhibits a different flower color, more compact growth habit, more flowers per plant, and more attractive foliage than both of its parental varieties. Further, 'BullEchipur 1201' exhibits larger flowers than its male parent.

When 'BullEchipur 1201' is compared to *Echinacea purpurea* variety named 'PAS702917' (unpatented, marketed as "PowWow® Wild Berry"), 'BullEchipur 1201' is similar to 'PAS702917' in botanical classification, but 'BullEchipur 1201' exhibits a different flower color with more flowers per plant, more compact and uniform growth with increased branching, and more healthy, dark green foliage that distinguish it from 'PAS702917'. Further, the following characteristics distinguish 'BullEchipur 1201' when generally compared to other *Echinaces* varieties known to the breeder:

Wine red flower color;
High flower number per plant;
A compact and uniform growth habit;
High branching;
Fast crop time; and
Healthy, dark green foliage.

The new variety has been trial and field tested and has been found to retain its distinctive characteristics and remain true to type through successive asexual propagations. The present invention has not been evaluated under all possible environmental conditions. The phenotype may vary with variations in environment without a change in the genotype of the plant.

DESCRIPTION OF THE DRAWINGS

The accompanying photographic drawings illustrate the new variety at 22 weeks of age, with the color being as nearly true as is possible with color illustrations of this type.

DESCRIPTION OF THE PLANT

Figure 1:
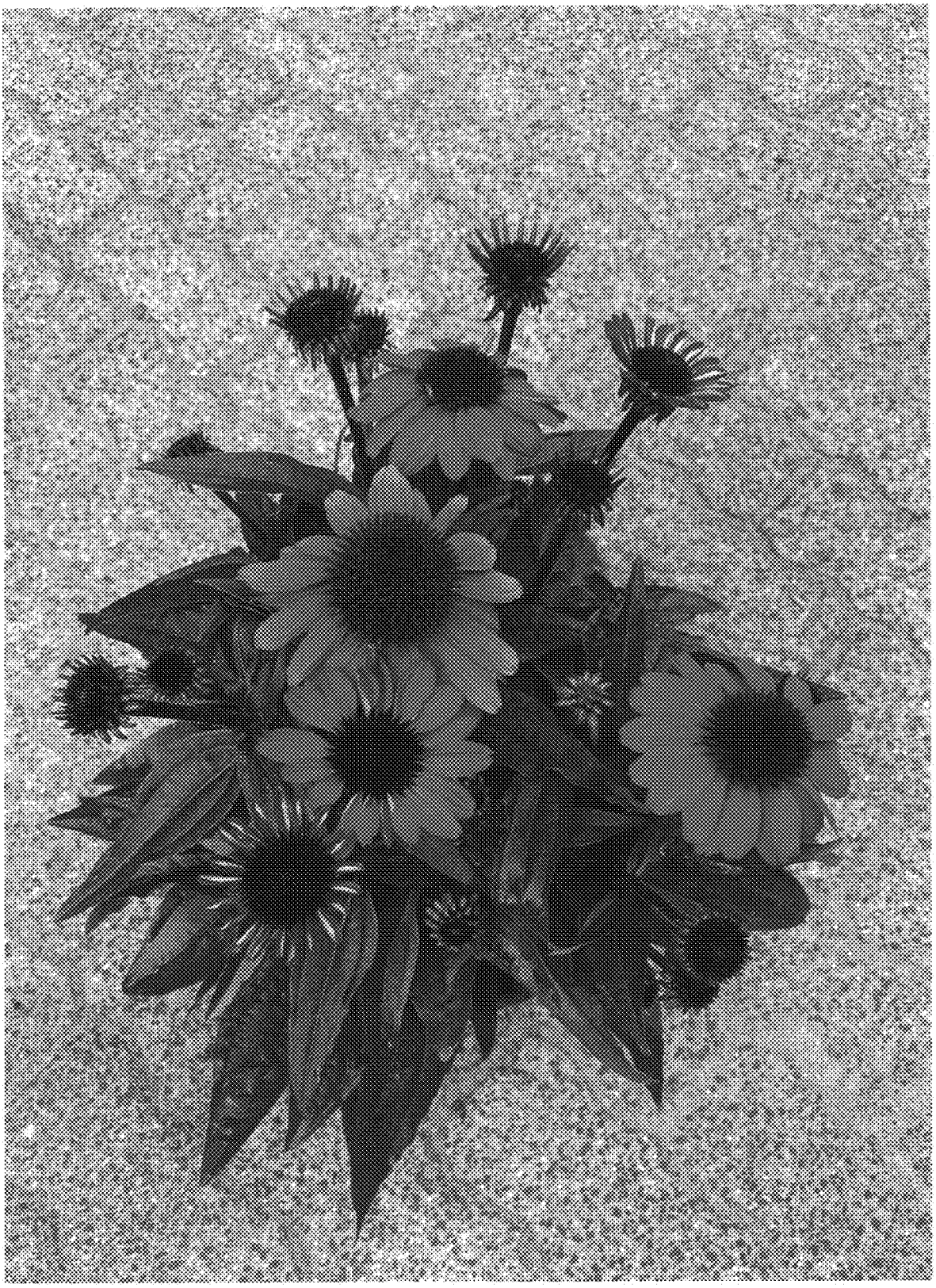
FIG. 1 shows an entire plant of the new variety.
Figure 2:
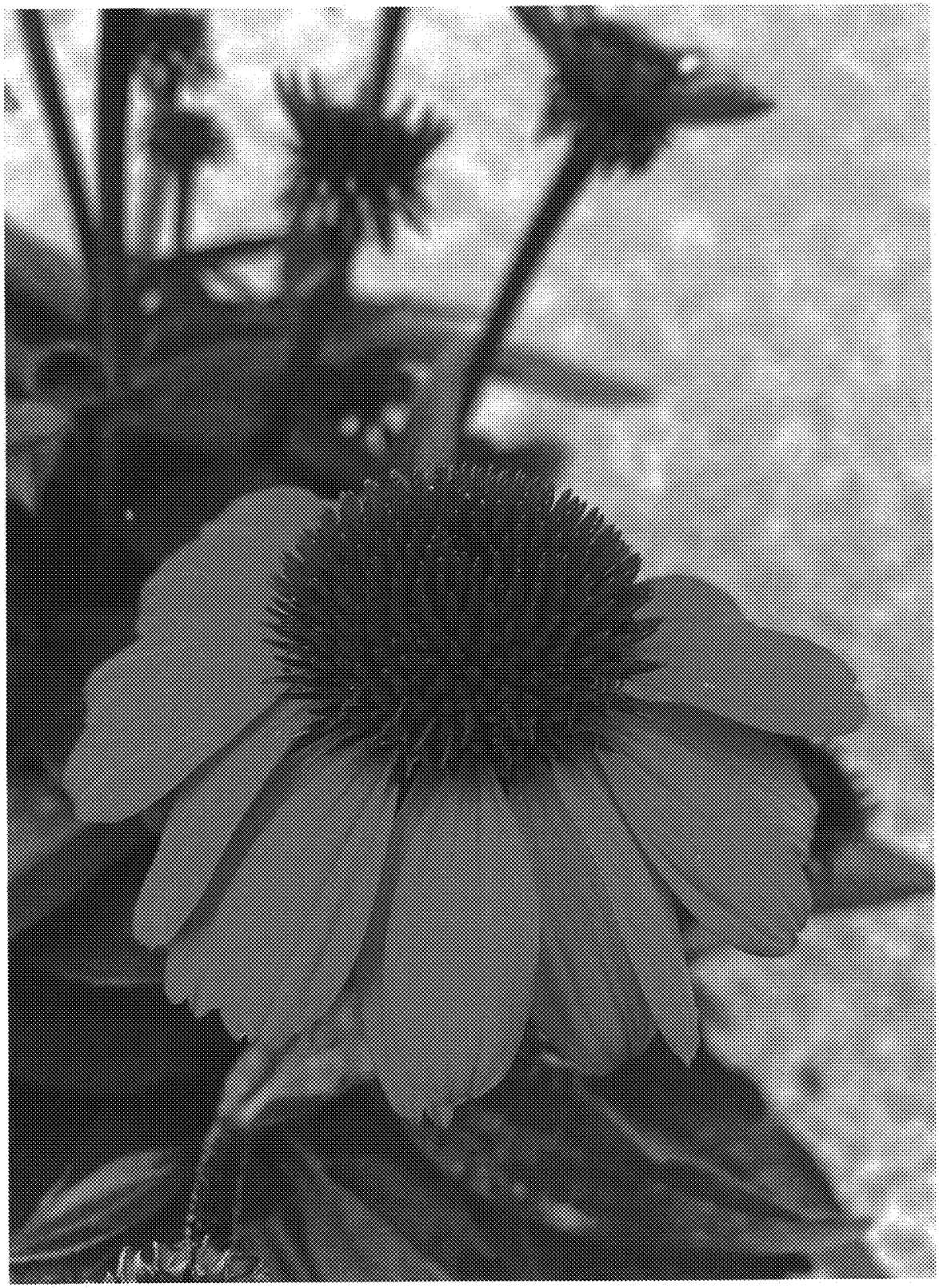
FIG. 2 shows a close-up view of a bloom of the new variety.
Figure 3:
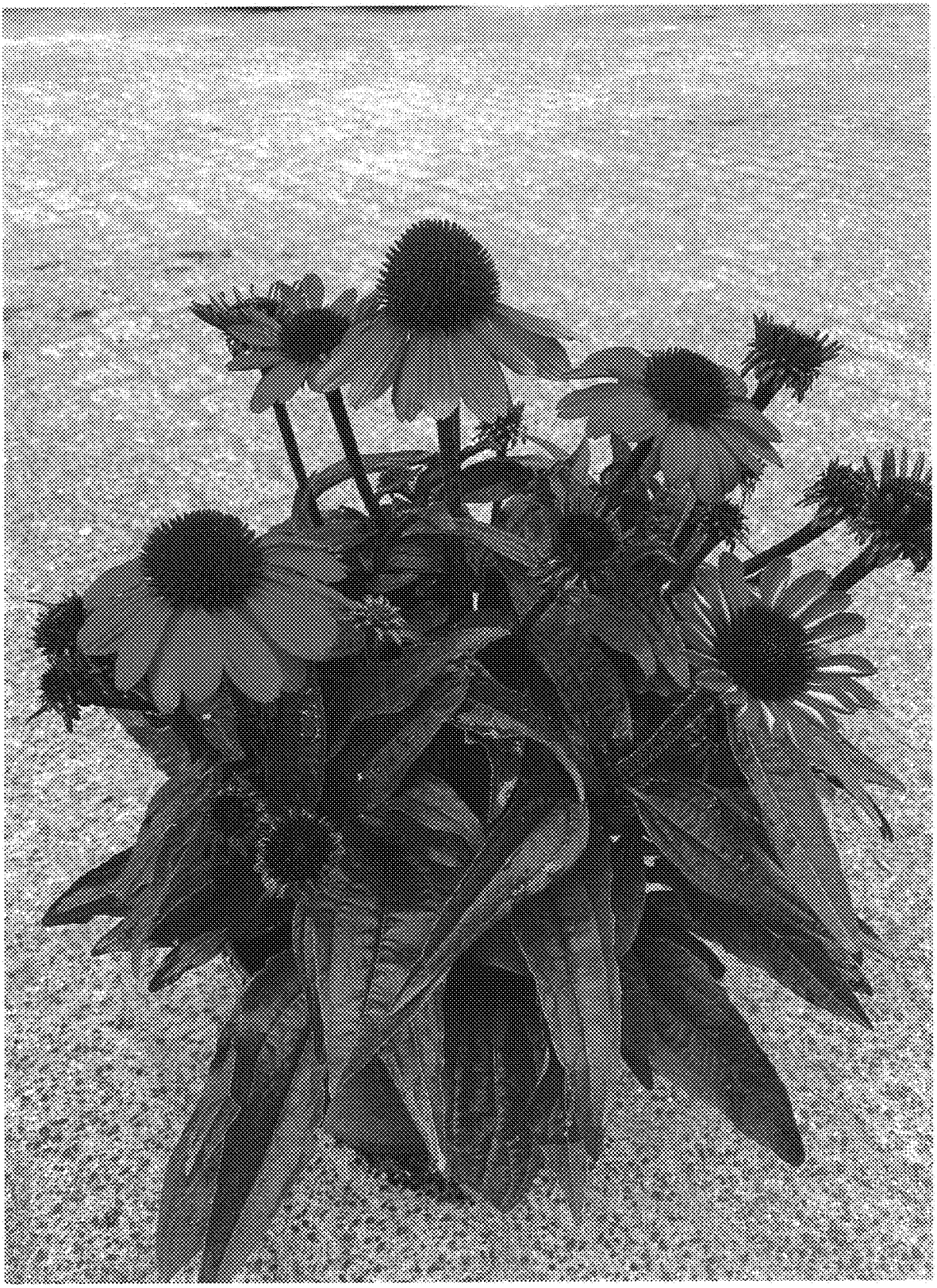
FIG. 3 shows an entire plant of the new variety.

The following detailed description sets forth the characteristics of the new variety as the result of asexual reproductions performed via in vitro tissue culture cuttings carried out in Gönnebeck, Germany. Plants of the new variety were grown outdoors in 19 cm (3 liter) pots under normal field production conditions, and the color readings and measurements were observed outdoors under natural light on 22 week old plants in Gönnebeck, Germany. Color references are primarily to The 2015 R.H.S. Colour Chart of The Royal Horticultural Society of London, Sixth Edition, except where terms of ordinary significance are used.

PLANT

Time to initiate roots: About 7 days at approximately 19-20° C.

*Time to develop roots.*—About 40-45 days at approximately 18° C.

*Time to produce a finished flowering plant from a rooted cutting.*—About 12-14 weeks in a 19 cm container.

*Rooting habit.*—Exhibits numerous roots that are freely branching and healthy in appearance.

*Plant height.*—35.0-50.0 cm.

*Plant width.*—30.0-40.0 cm.

*Habit.*—Upright, compact, and uniform growth with numerous branches.

*Disease/pest resistance.*—Nothing unusual noted to date.

*Temperature tolerance.*—Nothing unusual noted to date.

*Drought tolerance.*—Average.

*Branches (flowering stems).*—Number per plant: 20-35. Length: 20.0-35.0 cm. Diameter: 3.0-7.0 mm. Internode length: 1.0-6.0 cm. Angle: Upright and outward. Strength: Strong. Texture: Pubescence present. Color: Close to Yellow-Green Group RHS 144A up to Greyed-Orange Group RHS 177A.

*Foliage.*—Arrangement: Single. Leaf: Length: 4.0-25.0 cm. Width: 1.0-10.0 cm. Shape: Lanceolate. Apex: Acuminate. Base: Attenuate to acute. Margin: Entire. Aspect: Straight to curved. Texture: Upper surface: Rough. Lower surface: Rough. Color: Young leaves: Upper surface: Close to Green Group RHS 137A. Lower surface: Close to Green Group RHS 137C. Mature leaves: Upper surface: Close to Green Group RHS 137A. Lower surface: Close to Green Group RHS 137C. Petiole: None present. Veins: Venation type: Cross-venulate to longitudinal. Color: Upper surface: Close to Yellow-Green Group RHS 145B to Greyed-Purple Group RHS 186B. Lower surface: Close to Yellow-Green Group RHS 145B.

INFLORESCENCE

Bud:

*Diameter.*—0.7-3.0 cm.

*Length.*—1.5-2.0 cm.

*Color.*—Close to Green Group RHS N138B to Greyed-Purple Group RHS 187A.

*Appearance.*—Elliptic-shaped ray florets and tubular-shaped disc florets.

*Natural flowering season.*—Flowering occurs from July-September in Gönnebeck, Germany, beginning approximately 12-14 weeks after planting.

*Average number of inflorescences per plant.*—20-40.

*Average number of inflorescences per branch.*—2-4.

*Disc and ray floret arrangement.*—Disc florets are arranged in the middle of the receptacle of the composite, single, freely flowering plant, with ray florets extending outwardly therefrom.

*Fragrance.*—Unchanging.

*Inflorescence.*—Diameter: 5.0-10.0 cm. Height (depth): 2.0-4.0 cm. Diameter of disc: 2.0-4.5 cm. Receptacle height: 1.0 cm. Receptacle diameter: 2.0-3.5 cm.

*Ray florets.*—Number per inflorescence: 22-30. Arrangement: In two or three whorls. Length: 2.0-3.5 cm. Width: 1.3-8.0 cm. Shape: Elliptical. Apex: Obtuse. Base: Acute. Margin Entire. Texture: Upper surface: Smooth and glabrous. Lower surface: Rough. Color: When opening: Upper surface: Close to Red Group RHS 47A. Lower surface: Close to Red-Purple Group RHS 64C. At maturity: Upper surface: Close to Red-Purple Group RHS 60B. Lower surface: Close to Red-Purple Group RHS 64C. Ground color description: Close to Red-Purple Group RHS 60B. Venation: Appearance: Parallel. Color: Upper surface: Same color as the florets. Lower surface: Same color as the florets.

*Disc florets.*—Number per inflorescence: Numerous; too many to quantify. Arrangement: In the center of receptacle. Length: 10.0-15.0 mm. Width: 1.0-2.0 mm. Shape: Tubular. Apex: Pointed. Color: Immature: Close to Greyed-Purple Group RHS 187A. At maturity: Close to Greyed-Purple Group RHS 187A.

*Phyllaries.*—Number per inflorescence: 45-55. Arrangement: In four whorls. Length: Approximately 1.0 cm. Width: 3.0-4.0 mm. Shape: Lanceolate. Apex: Elongated oval. Base: Fused. Margin: Entire. Texture: Upper surface: Rough. Lower surface: Rough. Color: Immature: Upper surface: Close to Green Group RHS NN137C. Lower surface: Close to Green Group RHS NN137C. At maturity: Upper surface: Close to Green Group RHS NN137C. Lower surface: Close to Green Group RHS NN137C.

Reproductive organs:

*Androecium.*—Presence: On disc and ray florets. Number (per floret): Numerous. Filament length: 1.0-2.0 mm. Filament color: Close to Greyed-Purple Group RHS 187B. Anther: Shape: Oval. Length: 1.0 mm. Color: Close to Greyed-Purple Group RHS 187B. Pollen: Color: Close to Yellow-Orange Group RHS 15B. Amount: Plentiful — too much to quantify.

*Gynoecium.*—Presence: On disc florets. Pistil length: 2.0 mm. Stigma: Shape: Two-parted. Color: Close to Greyed-Purple Group RHS 187B. Style: Length: 1.0-2.0 mm. Color: Close to Greyed-Purple Group RHS 187B.

Seeds:

*Overall size.*—1.0-2.0 mm.

I claim:

1. A new and distinct variety of *Echinacea* plant named 'BullEchipur 1201', as is herein illustrated and described.

* * * * *